US009180263B2

(12) United States Patent
Gumaste et al.

(10) Patent No.: US 9,180,263 B2
(45) Date of Patent: Nov. 10, 2015

(54) LABORATORY ANIMAL PULMONARY DOSING DEVICE

(75) Inventors: Anand Gumaste, West Windsor, NJ (US); Scott Fleming, Ewing, NJ (US); Philip Chan, Hightstown, NJ (US)

(73) Assignee: MICRODOSE THERAPEUTX, INC., Monmouth Junction, NJ (US)

( * ) Notice: Subject to any disclaimer, the term of this patent is extended or adjusted under 35 U.S.C. 154(b) by 271 days.

(21) Appl. No.: 12/828,211

(22) Filed: Jun. 30, 2010

(65) Prior Publication Data

US 2011/0000482 A1 Jan. 6, 2011

Related U.S. Application Data

(60) Provisional application No. 61/222,433, filed on Jul. 1, 2009.

(51) Int. Cl.
*A61M 15/00* (2006.01)
*A61M 11/02* (2006.01)
(Continued)

(52) U.S. Cl.
CPC .................. *A61M 11/02* (2013.01); *A61D 7/04* (2013.01); *A61M 11/005* (2013.01); *A61M 15/001* (2014.02); *A61M 15/0085* (2013.01); *A61M 15/0083* (2014.02); *A61M 2016/0024* (2013.01); *A61M 2016/0027* (2013.01); *A61M 2016/0042* (2013.01); *A61M 2016/103* (2013.01); *A61M 2016/1035* (2013.01);
(Continued)

(58) Field of Classification Search
CPC ......... A61D 7/00; A61D 7/04; A01K 1/0047; A01K 1/0064; A01K 1/03; A01K 1/031; A01K 1/0613; A61M 11/005; A61M 11/02; A61M 11/04; A61M 15/005; A61M 15/001; A61M 15/0011; A61M 15/0021; A61M 15/0028; A61M 15/003; A61M 15/0065; A61M 15/0083; A61M 15/0085; A61M 15/0086; A61M 15/0091; A61M 15/08; A61M 15/085; A61M 16/104; A61M 16/1045; A61M 16/105; A61M 16/1065; A61M 16/18; A61M 2250/00
USPC ............. 128/200.14, 200.16, 203.12–203.15, 128/203.21, 203.26, 203.27, 203.29; 119/416–420
See application file for complete search history.

(56) References Cited

U.S. PATENT DOCUMENTS 2,517,482 A 8/1950 Hall
3,507,277 A 4/1970 Altounyan et al.
(Continued)

FOREIGN PATENT DOCUMENTS

JP H09187192 7/1997 ............. A01K 67/00
WO WO 97/26934 7/1997
(Continued)

OTHER PUBLICATIONS

PCT Intl Search Report and Written Opinion, PCT/US10/40822, dated Aug. 17, 2010, (8 pgs).
(Continued)

*Primary Examiner* — Justine Yu
*Assistant Examiner* — Michael Tsai
(74) *Attorney, Agent, or Firm* — Hayes Soloway P.C.

(57) ABSTRACT

A laboratory animal pharmaceutical testing device comprising a substantially closed animal holding cell, having a dry powder generator communicating through a wall of the cell, and one or more filtered inlets for permitting exchange of fresh air into the cell.

23 Claims, 3 Drawing Sheets

(51) Int. Cl.
*A61D 7/04* (2006.01)
*A61M 11/00* (2006.01)
*A61M 16/00* (2006.01)
*A61M 16/10* (2006.01)

(52) U.S. Cl.
CPC ............... *A61M 2202/0225* (2013.01); *A61M 2202/0275* (2013.01); *A61M 2202/064* (2013.01); *A61M 2205/3368* (2013.01); *A61M 2205/50* (2013.01); *A61M 2205/581* (2013.01); *A61M 2205/582* (2013.01); *A61M 2205/583* (2013.01); *A61M 2205/84* (2013.01); *A61M 2230/432* (2013.01); *A61M 2230/437* (2013.01); *A61M 2230/50* (2013.01); *A61M 2230/63* (2013.01); *A61M 2250/00* (2013.01)

(56) References Cited

U.S. PATENT DOCUMENTS

| | | | |
|---|---|---|---|
| 3,518,992 A | 7/1970 | Altounyan et al. | |
| 3,635,219 A | 1/1972 | Altounyan et al. | 128/266 |
| 3,653,380 A | 4/1972 | Hansen | 128/203.15 |
| 3,795,244 A | 3/1974 | Lax et al. | 128/266 |
| 3,807,400 A | 4/1974 | Cocozza | 128/266 |
| 3,831,606 A | 8/1974 | Damani | 128/266 |
| 3,948,264 A | 4/1976 | Wilke et al. | 128/203.15 |
| 3,991,304 A * | 11/1976 | Hillsman | 600/538 |
| 4,094,317 A | 6/1978 | Wasnich | 128/200.16 |
| 4,240,418 A | 12/1980 | Rosskamp et al. | 128/203.15 |
| 4,402,315 A | 9/1983 | Tsuda et al. | 128/200.18 |
| 4,448,150 A * | 5/1984 | Catsimpoolas | 119/455 |
| 4,452,239 A | 6/1984 | Malem | 128/200.17 |
| RE32,113 E * | 4/1986 | Harr | 119/419 |
| 4,721,060 A | 1/1988 | Cannon et al. | 119/15 |
| 4,860,741 A * | 8/1989 | Bernstein et al. | 128/204.18 |
| 4,938,209 A * | 7/1990 | Fry | 128/200.21 |
| 4,986,269 A * | 1/1991 | Hakkinen | 128/204.23 |
| 5,148,766 A * | 9/1992 | Coiro et al. | 119/418 |
| 5,152,284 A | 10/1992 | Valentini et al. | 128/203.21 |
| 5,260,321 A | 11/1993 | Hof et al. | 514/338 |
| 5,297,502 A | 3/1994 | Jaeger | 119/15 |
| 5,349,947 A | 9/1994 | Newhouse et al. | 128/203.21 |
| 5,429,302 A | 7/1995 | Abbott | 239/102.2 |
| 5,458,135 A | 10/1995 | Patton et al. | 128/200.14 |
| 5,479,920 A * | 1/1996 | Piper et al. | 128/204.23 |
| 5,497,763 A | 3/1996 | Lloyd et al. | 128/200.14 |
| 5,509,406 A * | 4/1996 | Kock et al. | 128/203.14 |
| 5,694,920 A | 12/1997 | Abrams et al. | 128/200.16 |
| 5,699,649 A | 12/1997 | Abrams et al. | 53/428 |
| 5,724,959 A | 3/1998 | McAughey et al. | 128/203.15 |
| 5,727,546 A | 3/1998 | Clarke et al. | 128/203.15 |
| 5,740,793 A | 4/1998 | Hodson et al. | 128/203.15 |
| 5,758,823 A | 6/1998 | Glezer et al. | 239/4 |
| 5,823,434 A | 10/1998 | Cooper | 239/102.2 |
| 5,853,002 A | 12/1998 | Kawasaki | 128/200.14 |
| 5,894,990 A | 4/1999 | Glezer et al. | 239/423 |
| 5,908,158 A | 6/1999 | Cheiman | 239/102.2 |
| 5,938,118 A | 8/1999 | Cooper | 239/102.2 |
| 5,954,049 A | 9/1999 | Foley et al. | 128/203.29 |
| 6,026,809 A | 2/2000 | Abrams et al. | 128/203.15 |
| 6,142,146 A | 11/2000 | Abrams et al. | 128/203.15 |
| 6,152,130 A | 11/2000 | Abrams et al. | 128/204.21 |
| 6,209,538 B1 | 4/2001 | Casper et al. | 128/203.15 |
| 6,294,582 B1 | 9/2001 | Jerussi | |
| 6,312,909 B1 | 11/2001 | Shyjan | 435/6 |
| 6,328,033 B1 | 12/2001 | Avrahami | 128/203.15 |
| 6,347,629 B1 | 2/2002 | Braithwaite | 128/203.15 |
| 6,352,076 B1 * | 3/2002 | French | 128/203.12 |
| 6,415,790 B1 | 7/2002 | Leedom et al. | 128/203.15 |
| 6,457,654 B1 | 10/2002 | Glezer et al. | 239/4 |
| 6,523,538 B1 * | 2/2003 | Wikefeldt | 128/204.18 |
| 6,526,966 B1 | 3/2003 | Peesay | 128/200.21 |
| 6,536,427 B2 | 3/2003 | Davies et al. | 128/203.15 |
| 6,543,442 B2 | 4/2003 | Gonda et al. | 128/200.14 |
| 6,622,720 B2 | 9/2003 | Hadimioglu | 128/200.16 |
| 6,698,425 B1 | 3/2004 | Widerstrom | 128/203.25 |
| 6,722,581 B2 | 4/2004 | Saddoughi | 239/102.2 |
| 6,759,159 B1 | 7/2004 | Gray et al. | 429/71 |
| 6,776,158 B1 * | 8/2004 | Anderson et al. | 128/203.12 |
| 6,792,945 B2 | 9/2004 | Davies et al. | 128/203.15 |
| 6,840,239 B2 | 1/2005 | Myrman | |
| 6,871,647 B2 | 3/2005 | Allan et al. | 128/203.21 |
| 6,889,690 B2 | 5/2005 | Crowder et al. | 128/203.15 |
| 6,904,912 B2 | 6/2005 | Roy et al. | 128/203.18 |
| 6,948,496 B2 * | 9/2005 | Eason et al. | 128/203.15 |
| 6,962,266 B2 | 11/2005 | Morgan et al. | 221/25 |
| 6,971,383 B2 | 12/2005 | Hickey et al. | 128/203.15 |
| 7,077,126 B2 | 7/2006 | Kummer et al. | 128/200.23 |
| 7,080,644 B2 | 7/2006 | Gumaste | 128/203.15 |
| 7,100,608 B2 * | 9/2006 | Brewer et al. | 128/204.23 |
| 7,231,920 B2 * | 6/2007 | Harvey et al. | 128/203.15 |
| 7,318,434 B2 | 1/2008 | Gumaste et al. | 128/203.15 |
| 7,334,577 B2 | 2/2008 | Gumaste et al. | 128/203.15 |
| 7,343,914 B2 | 3/2008 | Abrams et al. | 128/200.23 |
| 7,527,021 B2 | 5/2009 | Mead et al. | 119/420 |
| 7,784,429 B2 * | 8/2010 | Chiodo | 119/417 |
| 2002/0103443 A1 | 8/2002 | Roy et al. | 600/532 |
| 2003/0041859 A1 | 3/2003 | Abrams et al. | 128/200.22 |
| 2003/0062042 A1 | 4/2003 | Wensley et al. | 128/203.12 |
| 2003/0192540 A1 | 10/2003 | Myrman et al. | 128/203.15 |
| 2004/0263567 A1 | 12/2004 | Hess et al. | 347/47 |
| 2005/0026909 A1 | 2/2005 | Landau et al. | |
| 2005/0087189 A1 | 4/2005 | Crockford et al. | |
| 2005/0109659 A1 | 5/2005 | Hickey et al. | 206/538 |
| 2005/0172962 A1 | 8/2005 | Gumaste et al. | |
| 2005/0183724 A1 | 8/2005 | Gumaste et al. | 128/203.15 |
| 2006/0174869 A1 | 8/2006 | Gumaste et al. | |
| 2007/0060652 A1 | 3/2007 | Fraser et al. | |
| 2007/0119969 A1 | 5/2007 | Collins et al. | 239/102.1 |
| 2008/0035143 A1 * | 2/2008 | Sievers et al. | 128/203.12 |
| 2008/0047554 A1 * | 2/2008 | Roy et al. | 128/203.15 |
| 2008/0202514 A1 | 8/2008 | Kriksunov et al. | 128/203.15 |
| 2009/0000615 A1 | 1/2009 | Pohlmann et al. | 128/200.21 |
| 2009/0151720 A1 * | 6/2009 | Inoue et al. | 128/203.12 |
| 2009/0275810 A1 * | 11/2009 | Ayers et al. | 600/301 |
| 2010/0263666 A1 | 10/2010 | Nagata et al. | 128/203.14 |

FOREIGN PATENT DOCUMENTS

| | | | |
|---|---|---|---|
| WO | WO 98/32479 | 7/1998 | |
| WO | WO 99/64095 | 12/1999 | |
| WO | WO 99/65550 | 12/1999 | |
| WO | WO 00/71108 | 11/2000 | |
| WO | WO 03/039464 | 5/2003 | |
| WO | WO 2004/039763 | 5/2004 | |
| WO | WO 2006/047427 | 5/2006 | |
| WO | WO2008142786 | 11/2008 | ............ A61M 13/00 |

OTHER PUBLICATIONS

"Nebulizer", http://en.wikipedia.org/wiki/Nebulizer, Jun. 26, 2009, 2 pgs.
Translation of Japanese Office Action issued in corresponding application No. 2012-518613, dated Mar. 4, 2014 (2 pgs).
Extended European Search Report issued in related application No. 10794785.5, dated Apr. 2, 2014 (9 pgs).

* cited by examiner

FIG. 2

LABORATORY ANIMAL PULMONARY DOSING DEVICE

CROSS REFERENCE TO RELATED APPLICATION

This application claims priority from U.S. Provisional Application Ser. No. 61/222,433, filed Jul. 1, 2009, the contents of which are incorporated herein by reference.

BACKGROUND OF THE INVENTION

This invention relates to drug development, and more particularly to improvements in tools for conducting preclinical safety and efficacy studies in animals.

FIELD OF THE INVENTION

Drug development is a time-consuming and costly activity. Procedures are tightly regulated both for safety and to ensure drugs are effective. Of the many compounds studied with the potential to become a medicine, most are eliminated during the initial research phases. Chemical trials follow extensive research using in vitro and animal studies.

Animal studies are a vital part of drug development. Typically, a candidate drug is initially tested in isolated cells, tissue slices or organs. Studies in living animals show whether a drug works the same way inside the body as it did in the artificial environment of the laboratory. They also indicate how the drug effects interactions between different cells and organs of the body. If a potential drug appears to be both safe and effective in animals, it then can be studied in human trials.

Dry powder dosing of animals both for pharmacology and pulmonary toxicology studies are required steps in the development of dry powder inhaled therapies. In order to conduct these studies, dry powder therapeutics need to be aerosolized and delivered to the animals in a controlled, measurable and reproducible manner, and with a prescribed particle size distribution to: 1) screen potential compounds for their efficacy and safety when presented to the animal in a similar manner to humans, and 2) satisfy the FDA that the therapeutic is safe to be tested in man. Current dry powder aerosolization systems, representing state of the art, are relatively rudimentary and inefficient, and as such are highly wasteful of what in many cases is precious amounts of an active pharmaceutical ingredient. Furthermore, these aerosolization systems are certainly not reflective of the ultimate and intended commercial delivery device.

SUMMARY OF THE INVENTION

The present invention provides an improved system for conducting animal tests of active pharmaceutical ingredients. Previously, we have described a unique dry powder inhaler employing a vibratory mechanism for deaggregation and aerosolization of dry powder pharmaceuticals in a dry powder inhaler for delivery of carefully controlled particle size active pharmaceutical ingredients to the lungs of a patient. These same dry powder inhalers also advantageously may be employed to create a "cloud" of active pharmaceutical ingredients in a closed environment for inhalation by animals in preclinical animal testing. Also, these same dry powder inhalers may be used by manually activating the vibratory mechanism to create aerosol clouds in a pulsatile fashion in order to achieve a desirable dose of drug administered over a preselected time period or the manual activation may be replaced with automated activation of the aerosolization engine through sensing of the animal's inhalation or tidal breathing maneuver. The closed environment may include, but is not limited to, an animal holding cell or chamber in which the animal is placed inside for full body dosing, or a cell or chamber wherein the animal breathes in from dosing stations on the outside of the chamber, or direct tubing to the animal through a facemask or a nose-only mask or a nasal cannula, e.g. as described in my co-pending U.S. application Ser. No. 12/828,133, based on U.S. Provisional Application Ser. No. 61/222,418, filed contemporaneously herewith, and incorporated herein by reference).

BRIEF DESCRIPTION OF THE DRAWINGS

Further features and advantages of the instant invention will be seen from the following detailed description taken in conjunction with the accompanying drawings, wherein:

FIG. 2 illustrates a laboratory animal "nose-only" dosing apparatus in accordance with a second embodiment of the present invention.

DETAILED DESCRIPTION OF PREFERRED EMBODIMENTS

Figure 1:
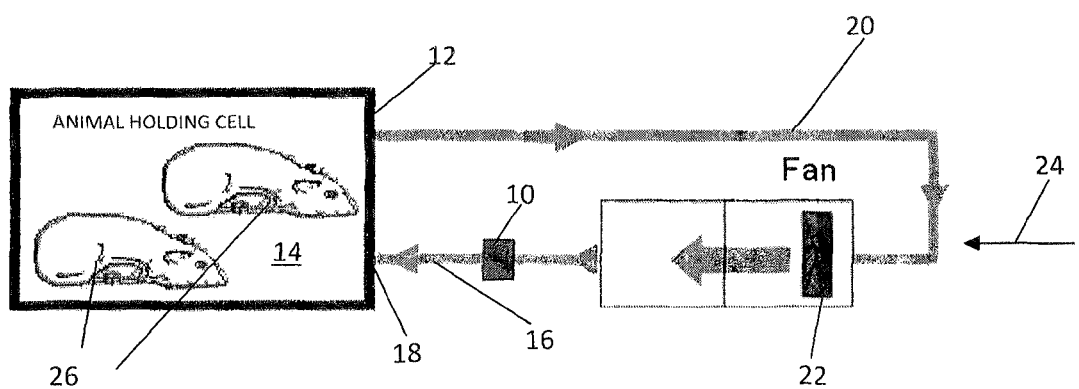
FIG. 1 illustrates a laboratory animal full body dosing apparatus in accordance with one embodiment of the present invention.

FIG. 1 illustrates an embodiment of the present invention wherein a pharmaceutical nebulizer 10 communicates through a side wall 12 of an animal holding cell 14. The nebulizer 10 preferably comprises a dry powder nebulizer and communicates via conduit 16 through an opening 18 in side wall 12 that forms an essentially airtight seal. In this embodiment, the opening 18 preferably is located in the upper part of animal holding cell 14 so that a cloud of powdered pharmaceutical will be injected into the upper part of cell 14 and the bulk of the powder will be inhaled by the animal or animals 26 in the cell 14 before the powder settles to the floor of the cell. In a preferred embodiment of the invention, air is recirculated from cell 14 via a conduit 20 and fan 22. In that way, unused medication is returned rather than wasted. If desired, one or more filtered inlets 24 may be provided for permitting introduction of fresh air into the enclosure without permitting escape of any of the powdered pharmaceutical ingredients.

The pharmaceutical nebulizer preferably comprises a vibratory dry powder inhaler, incorporating a high frequency piezo vibratoir, available from MicroDose Therapeutx, Inc. of Monmouth Junction, N.J. See U.S. patent, including Nos. 6,026,809, 6,142,146, 6,152,130, 7,318,434, 7,334,577, 7,343,914 and Published U.S. Application Nos. 2005/0172962 and 2008/0202514, all assigned to the common assignee.

Figure 2:
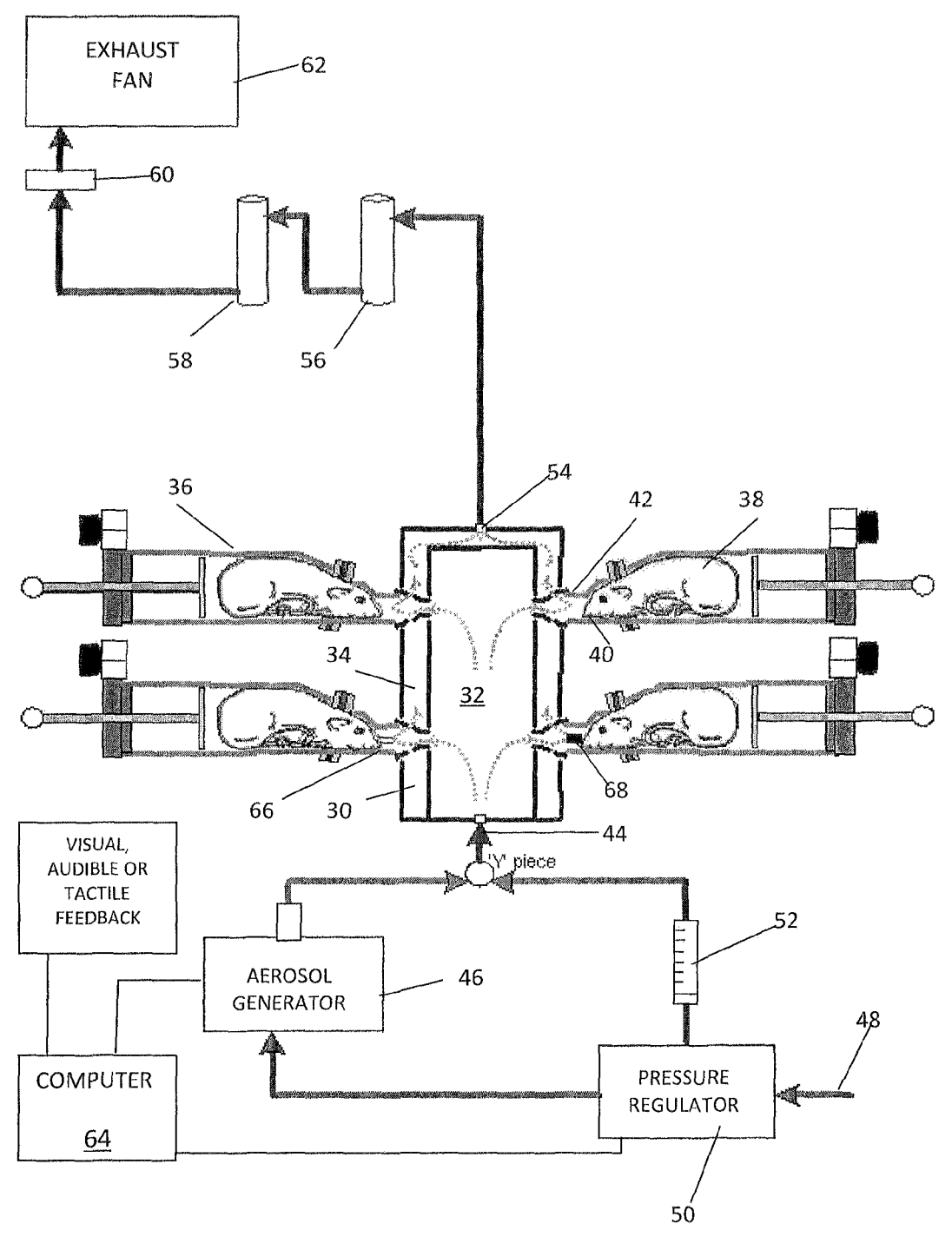

FIG. 2 illustrates an alternative embodiment of the present invention in which laboratory animals are restrained and medication delivered to the animals' nose or mouth. The laboratory animal "nose-only" dosing apparatus includes a dosing chamber 30 including a main chamber 32 and a side chamber 34 opening to animal holding chambers 36. The animal holding chambers 36 are sized to humanely restrain laboratory animals 38 with their mouths and noses 40 held in position in chambers 42 which essentially act as breathing masks. Alternatively, nasal cannulae 66 or mouthpieces 68 may be provided in chambers 42. Chambers 42 (or the nasal cannulae or mouthpieces as the case may be), communicate with side chambers 34 which in turn communicate with main chamber 32. Medication is introduced into main chamber 32 via an opening 44 and the lower end of the main chamber 32 as a cloud of powdered pharmaceutical which is carried to the animals via chambers 42. The cloud is created by sweeping dry powder aerosolized pharmaceutical created at a dry powder aerosol generator 46, and carried by pressurized carrier air stream from a pressurized air source 48. Air pressure is regulated by pressure regulator 50 and an optional flow controller 52.

The apparatus also preferably includes an outlet 54 located adjacent the top end of the dosing chamber 30 leading to a scrubber 56, a dryer 58 and filter 60 and exhaust fan 62 before being vented into the air. In this manner loss of pharmaceutical is minimized, and exposure of laboratory workers to the pharmaceutical is also minimized.

Figure 3:
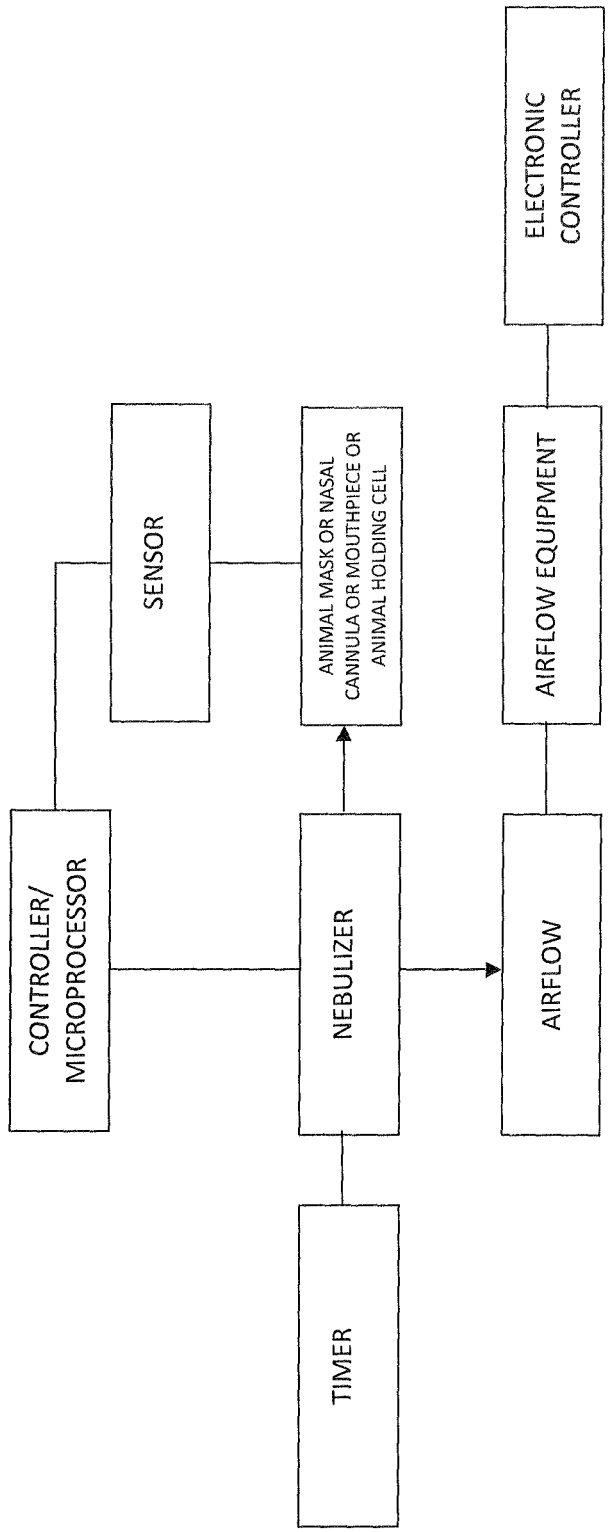
FIG. 3 illustrates yet another embodiment of the invention.

As is shown in FIG. 3, the device of any of the various embodiments of the invention may further comprise a controller for controlling a nebulizer that is in communication with an animal mask, nasal cannula, mouthpiece, or animal holding cell. The controller may, for example, turn the nebulizer on and off synchronized to tidal breathing of the animal. Accordingly, the device may further comprise a sensor for sensing an inhalation and/or exhalation cycle of an animal. The device or the controller may further comprise a microprocessor. The device may also comprise a timer for controlling the nebulizer. The device may further comprise an electronic controller for controlling airflow equipment that is connected to the nebulizer or animal mask, nasal cannula, mouthpiece, or animal holding cell.

Completing the system is a computer 64 for controlling airflow, duration and frequency of operation of the dry powder aerosol generator, the number of timed or pulsed activations of the vibrating element, etc. The system may also include visual, audible or tactile feedbacks to the equipment operation indicating the status of the device and dosing, etc.

In yet another embodiment of the invention, the nebulizer also may be triggered to turn on and off by sensing tidal breathing of the laboratory animal, and operate over one or several breaths, e.g., following the teachings of our aforesaid co-pending U.S. application Ser. No. 12/828,133, which is incorporated herein by reference. By way of example, as shown in FIGS. 6 and 7 of our aforesaid co-pending application, and in FIG. 3 of the instant application, the inhalation and/or exhalation cycle is sensed by a sensor and the aerosol generator is turned on for a short duration, and then off, followed by an amount of chase air to carry or follow the particles into the animal. A sufficient quantity of chase air is necessary to ensure lung deposition when inhalation volumes are low and inhalation cycles are short. Any sensor or combination of sensors that can be used to measure or identify the difference in properties between an inhalation and exhalation maneuver can be used to synchronize and turn the aerosol generator on and off. Examples of sensors that may be used to detect the animals' inhalation/exhalation are flow sensors, pressure sensors, temperature sensors that measure the temperature difference between the inhaled and exhaled breath, carbon dioxide or nitric oxide or other gas sensors that measure the gas component level difference between inhaled and exhaled breath, and also physical measurement systems such as chest straps to measure the expansion and contraction of the chest cavity, etc., can be employed for this purpose. The present invention provides several novel and significant advantages. A feature and advantage of the present invention is that the pharmaceutical nebulizer has an ability to provide greater accuracy, efficiency and reproducibility over current systems. Also, the invention permits delivery of carefully controlled pulmonary drug doses with a targeted and desired particle size distribution. The drug active ingredients may be delivered as a "neat" spray-dried or micronized drug, or lactose blend. Unlike existing laboratory animal testing chambers, laboratory animal testing devices in accordance with the present invention do not require in-line micronizers to maintain a target mass medium aerodynamic particle diameter. Thus, the present invention permits handling of extremely small quantities of drugs, reducing drug waste, and providing more controlled testing environment and greater consistency of dose delivery. Moreover, the systems described are directly reflective of the core system used in hand-held inhalers and dry nebulizers being developed for humans. Thus, administration of dry powder active pharmaceutical ingredients to laboratory animals using vibratory dry powder inhaler technology as described for animal testing more closely mimics delivery of the same active pharmaceutical ingredients in humans. Accordingly, by using essentially the same engine for delivering the dry powder active pharmaceutical ingredients to laboratory test animals as will be used in delivery to humans, scale of delivery through early pharmaceutical studies to toxicity in human trials is more predictable.

Various changes may be made in the above invention without departing from the spirit and scope thereof. For example, it is possible to control the amount of drug delivered to the nasal passages of the laboratory animal as opposed to just the lower respiratory track by controlling particle size. Still other change are possible. For example, referring to FIG. 3, in another embodiment, nebulized drugs may be administered to individual laboratory animal primates via tubing leading to face masks or nasal cannulae, and, if desired, dosing controlled, e.g. by sensing inhalation and exhalation, and turning the nebulizer on and off as described above relative to the other embodiments.

The invention claimed is:

1. A laboratory animal pharmaceutical testing device comprising a substantially closed animal holding cell sized to accommodate more than one animal at the same time;
   a vibratory dry powder generator communicating through an opening in a wall of the cell for introduction of a medication into the cell;
   one or more filtered inlets for permitting exchange of fresh air into the cell; and
   a conduit including a fan through which air and medication in the cell is recirculated out of the cell and returned to the cell;
   wherein the opening in the wall of the cell through which the medication is introduced into the cell is located in an upper part of the cell so that the bulk of the medication will be inhaled by the animals before the medication settles in the bottom of the cell, and
   wherein said cell and conduit are sealed such that air and nebulized medication inside the cell or conduit are not able to exit from the cell and conduit to the atmosphere outside of the cell and conduit.

2. The device of claim 1, wherein the vibratory dry powder generator comprises a piezo vibrator.

3. The device of claim 1, further comprising a microprocessor and control for the nebulizer.

4. The device of claim 1, further comprising a timer for controlling the nebulizer.

5. The device of claim 1, further comprising an electronic controller for controlling airflow equipment connected to the animal holding cell.

6. The device of claim 1, wherein a dose delivered amount is determined by the number of timed or pulsed activations of the nebulizer.

7. The device of claim 1, further comprising visual, audible or tactile feedbacks to the equipment operator indicating a status of the device and of dosing.

8. A device for delivering dry powder medication to laboratory animals, comprising an aerosol chamber into which an aerosolized medication may be introduced;
- an animal holding cell including a mask portion, wherein said animal holding cell is sized to restrain an animal's mouth and nose in position within the cell and wherein the mask portion includes a mouthpiece or nasal cannula;
- an outlet for said chamber in communication with said animal holding cell, wherein said outlet is at least partially surrounded by said mask portion;
- a nebulizer for aerosolizing a medication and introducing the medication into the chamber;
- a sensor for sensing an inhalation and/or exhalation cycle of the animal, and a controller for turning the nebulizer on and off synchronized to tidal breathing of the animal, and
- an exhaust fan, a filter, a scrubber and a dryer in communication with the aerosol chamber and also in communication with atmospheric air outside the device, wherein air carrying the aerosolized medication passes through the exhaust fan, filter, scrubber and dryer before being vented into the outside atmospheric air so that loss of medication from the device is minimized; and a conduit including the fan through which air and medication in the cell is recirculated out of the cell and returned to the cell.

9. The device of claim 8, further comprising a microprocessor and control for the nebulizer.

10. The device of claim 8, further comprising a timer for controlling the nebulizer.

11. The device of claim 8, further comprising an electronic controller for controlling airflow equipment connected to the chamber.

12. The device of claim 8, wherein a dose delivered amount is determined by the number of timed or pulsed activations of the nebulizer.

13. The device of claim 8, further comprising visual, audible or tactile feedbacks to the equipment operator indicating the status of the device and of dosing.

14. The device of claim 8, wherein inhalation and/or exhalation is sensed using sensors selected from the group consisting of flow sensors, pressure sensors, temperature sensors, gas sensors and chest straps.

15. A laboratory animal pharmaceutical testing device comprising at least one animal holding chamber sized to restrain a laboratory animal with its mouth and nose held in position;
- a first chamber and a second chamber, wherein said first chamber and said second chamber are each in communication with said holding chamber;
- a pharmaceutical nebulizer communicating through said first chamber to said holding chamber;
- a controller for controlling the nebulizer;
- a sensor for sensing an inhalation and/or exhalation cycle of the animal, and a controller for turning the nebulizer on and off synchronized to tidal breathing of the animal;
- a pressurized air source in communication with the nebulizer and capable of producing a positive pressure air stream to deliver a medication from the nebulizer to the mask or nasal cannula section; and
- an exhaust fan, a filter, a scrubber and a dryer in communication with an outlet in said second chamber and also in communication with atmospheric air outside the device, wherein air carrying the medication passes through the exhaust fan, filter, scrubber and dryer before being vented into the outside atmospheric air so that loss of medication from the device is minimized; and a conduit including the fan through which air and medication in the cell is recirculated out of the at least one animal holding chamber and returned to the cell.

16. The device of claim 15, wherein the nebulizer comprises a vibratory dry powder inhaler.

17. The device of claim 16, wherein the vibratory dry powder inhaler comprises a piezo vibrator.

18. The device of claim 15, further comprising a microprocessor and control for the nebulizer.

19. The device of claim 15, wherein the controller comprises a microprocessor.

20. The device of claim 15, further comprising an electronic controller for controlling airflow equipment connected to the nebulizer.

21. The device of claim 15, wherein a dose delivered amount is determined by the number of timed or pulsed activations of the nebulizer.

22. The device of claim 15, further comprising visual, audible or tactile feedbacks to the equipment operator indicating the status of the device and of dosing.

23. The device of claim 15, wherein inhalation and/or exhalation is sensed using sensors selected from the group consisting of flow sensors, pressure sensors, temperature sensors, gas sensors and chest straps.

* * * * *